United States Patent
Bryan (10) Patent No.: US 7,722,645 B2
(45) Date of Patent: May 25, 2010

(54) PEDICLE SCREW SPINAL FIXATION DEVICE

(76) Inventor: Donald W. Bryan, 6151 S. Woodland Dr., Ogden, UT (US) 84403

( * ) Notice: Subject to any disclaimer, the term of this patent is extended or adjusted under 35 U.S.C. 154(b) by 2127 days.

(21) Appl. No.: 10/075,795

(22) Filed: Feb. 13, 2002

(65) Prior Publication Data

US 2003/0060823 A1 Mar. 27, 2003

Related U.S. Application Data

(60) Provisional application No. 60/324,660, filed on Sep. 24, 2001.

(51) Int. Cl.
*A61B 17/70* (2006.01)
(52) U.S. Cl. ..................... 606/246; 606/277
(58) Field of Classification Search .......... 606/61, 606/69, 72, 73, 105, 246, 250–253, 259, 606/261, 264–267, 270, 272, 277–280, 286, 606/300, 301, 305, 308, 319, 324, 328; 403/7, 403/118, 204; 411/18, 426
See application file for complete search history.

(56) References Cited

U.S. PATENT DOCUMENTS

| | | | |
|---|---|---|---|
| 4,653,481 A | 3/1987 | Howland et al. |
| 4,887,595 A | 12/1989 | Heinig et al. |
| 4,920,959 A | 5/1990 | Witzel et al. |
| 5,030,220 A | 7/1991 | Howland |
| 5,122,131 A | 6/1992 | Tsou |
| 5,129,900 A | 7/1992 | Asher et al. |
| 5,154,719 A | 10/1992 | Cotrel |
| 5,171,279 A | 12/1992 | Mathews |
| 5,190,543 A | 3/1993 | Schläpfer |
| 5,217,497 A | 6/1993 | Mehdian |
| 5,219,349 A | 6/1993 | Krag et al. |
| 5,242,445 A | 9/1993 | Ashman |
| 5,261,907 A | 11/1993 | Vignaud et al. |
| 5,282,862 A | 2/1994 | Baker et al. |
| 5,306,275 A | 4/1994 | Bryan |
| 5,344,422 A | 9/1994 | Frigg |
| 5,352,225 A | 10/1994 | Yuan et al. |
| 5,360,429 A | 11/1994 | Jeanson et al. |
| 5,380,325 A | 1/1995 | Lahille et al. |
| 5,437,669 A | 8/1995 | Yuan et al. |

(Continued)

FOREIGN PATENT DOCUMENTS

EP 0 553 424 A1 8/1993

(Continued)

*Primary Examiner*—Eduardo C Robert
*Assistant Examiner*—David Comstock
(74) *Attorney, Agent, or Firm*—Clayton, Howarth & Cannon, P.C.

(57) ABSTRACT

A spinal fixation device and method including at least one longitudinal rod mounted substantially parallel to the axis of the spine and having a plurality of stem clamps adjustably mounted to the longitudinal rod. Each stem clamp has a stem extending outwardly therefrom with the diameter of the stem being identical to the diameter of the longitudinal rod. A plurality of C-clamps are provided and are mounted to the stems and to the longitudinal rods. Each C-clamp includes a female-tapered through-passage for matingly engaging a male tapered head of a pedicle screw. A plurality of pedicle screws are used to simultaneously anchor the C-clamps to the bone and to the respective stem and longitudinal rod.

16 Claims, 9 Drawing Sheets

U.S. PATENT DOCUMENTS

| | | |
|---|---|---|
| 5,520,689 A | 5/1996 | Schläpfer et al. |
| 5,540,690 A | 7/1996 | Miller et al. |
| 5,545,228 A | 8/1996 | Kambin |
| 5,613,968 A | 3/1997 | Lin |
| 5,643,260 A | 7/1997 | Doherty |
| 5,716,355 A * | 2/1998 | Jackson et al. .............. 606/252 |
| 5,938,663 A | 8/1999 | Petreto |
| 5,947,965 A * | 9/1999 | Bryan ...................... 606/86 A |
| 5,947,967 A | 9/1999 | Barker |
| 5,984,922 A | 11/1999 | McKay |
| 6,123,706 A | 9/2000 | Lange |
| 6,187,005 B1 | 2/2001 | Brace et al. |
| 6,251,112 B1 | 6/2001 | Jackson |
| 6,562,040 B1 * | 5/2003 | Wagner ...................... 606/264 |

\* cited by examiner

PEDICLE SCREW SPINAL FIXATION DEVICE

CROSS-REFERENCE TO RELATED APPLICATIONS

This application claims the benefit of U.S. Provisional Application No. 60/324,660, filed Sep. 24, 2001, which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates generally to a spinal fixation system, and more particularly, but not necessarily entirely, to a surgical device capable of immobilizing at least one vertebra of the spine, fusing a portion of the spinal column.

2. Description of Related Art

The spine is a flexible, multi-segmented column that supports the upright posture in a human while providing mobility to the axial skeleton. The lumbar spine serves the functions of encasing and protecting vital neural elements and provides structural support for the body by transmitting the weight of the body through the pelvis to the lower extremities. Because there are no ribs attached to the lumbar spine, it has a relatively wide range of motion.

The spine is made up of bone, intervertebral discs, synovial joints with their articular cartilage, synovial capsules and, as part of the back, is surrounded by supporting ligaments, muscle, fascia, blood vessels, nerves, and skin. As in other areas of the body, these elements are subject to a variety of pathological disturbances: inflammation, trauma, neoplasm, congenital anomalies, disease, etc. In fulfilling its role in the back, the spine can be subjected to significant trauma which plays a dominant role in the etiology of low back pain. Trauma frequently results in damage at the upper end of the lumbar spine, where the mobile lumbar segments join the less mobile dorsal spine. Excessive forces on the spine not only produce life-threatening traumatic injuries, but may contribute to an increased rate of degenerative change. Degenerative changes tend to develop in the lower lumbar intervertebral discs, most commonly in the third decade. Osteoarthritis produces changes in the facet joints by middle age.

Stabilization of the spine is one method used to treat trauma, tumors, disabling pain, neurological compromise, deformity or degenerative pathologies. Many methods and devices have been used to improve the stabilization of the spine, such as implantation of rods positioned parallel to the spinous process using polyaxial screws, pedicle screws or other types of bone screws, which attach a connector to the rod. Other methods have been used to accomplish stabilization of the spine. However, a recurrent problem for spinal fixation is the differing anatomy of each patient, which creates a challenge for effectively attaching the requisite instrumentation to bone of the spine.

Attempts have been made in the prior art to provide alternatives for attaching instrumentation to the spine. U.S. Pat. No. 5,613,968 (granted Mar. 25, 1997 to Lin) discloses an orthopedic fixation device using a fixation ring, a universal pad, a threaded fixation element, and a fastening nut. This device is characterized by several disadvantages, including the many individual pieces that must be attached by a surgeon prior to implantation. The device is designed such that a limited degree of movement in the bone screw may be achieved through articulation between an arcuate washer and a universal pad, which does not serve to create a locking fit.

There are several other spinal fixation devices with differing modes of attachment known in the prior art, such as that disclosed in U.S. Pat. No. 5,938,663 (granted Aug. 17, 1999 to Petreto). This patent reference discloses a spinal instrument for adjustable connecting rods comprising a nut that clamps to a receiving and locking assembly. The device has a ball joint used for angularly connecting the rod to the receiving and locking assembly, however, this device is characterized by a limited range of motion, which is not advantageous for complex anatomical situations.

U.S. Pat. No. 6,123,706 (granted Sep. 26, 2000 to Lange) discloses a support system for stabilizing the spine for surgical treatment which requires spinal fixation. The device provides for a bone screw to have a limited range of motion and utilizes a nut to fasten and lock the device. Disadvantageously, the device utilizes several component parts to create a locking mechanism to fix a bone screw at differing angles.

U.S. Pat. No. 6,187,005 (granted Feb. 13, 2001 to Brace et al.) discloses a variable angle spinal fixation system which includes a longitudinal member, a threaded fastener, and a connector member for connecting the fastener. The device is characterized by a locking system, which is disadvantageous because of the number of component parts increasing the complexity of the system, including inserting a polyaxial screw into a threaded skirt, which in turn is inserted into the connector to create a lock. Additionally, the polyaxial screw portion creates an overly large profile system which has the potential for discomfort when implanted onto a patient's spine.

The prior art is thus characterized by several disadvantages that are addressed by the present invention. The present invention minimizes, and in some aspects eliminates, the above-mentioned failures, and other problems, by utilizing the methods and structural features described herein.

It is noteworthy that none of the references in the art known to applicant provides a spinal fixation device providing a pedicle screw having a variety of attachment angles with a low profile, and a locking system utilizing a pedicle screw and a clamp forming a morse taper locking fit. There is a long felt, but unmet, need for a spinal fixation device that has a low profile, is easily assembled, is relatively inexpensive to make, and simple in operation.

The prior references in the art relating to spinal fixation devices utilize various mechanical features for enabling the surgeon to selectively adjust the alignment of the patient's spine and then to secure that alignment with the locking of the spinal fixation device to the spine. Most of these devices are relatively difficult to adjust and require undue surgical time in their implantation. Further, due to the wide variation in spinal dimensions and availability of suitable attachment sites, most devices have limited application. Further still, these devices do not allow the surgeon to easily manipulate and position the bone screws prior to final tightening of the device.

In view of the foregoing, it would be a significant advancement in the art to provide a spinal fixation apparatus and method that was highly modular and interchangeable, simplified, and would increase the ease of installation and adjustment while decreasing the total time required for surgical implantation and fixation. Such a novel spinal fixation apparatus and method is disclosed and claimed herein.

BRIEF DESCRIPTION OF THE DRAWINGS

The features and advantages of the invention will become apparent from a consideration of the subsequent detailed description presented in connection with the accompanying drawings in which:

FIG. 6 through FIG. 12 appear in sequential order and illustrate the spinal fixation device being implanted onto a spine in accordance with the principles of the present invention.

DETAILED DESCRIPTION OF THE INVENTION

For the purposes of promoting an understanding of the principles in accordance with the present invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present device and methods for surgically attaching a spinal fixation device to the vertebrae of the spine are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The invention is best understood from the following description with reference to the drawings wherein like parts are designated by like numerals throughout and taken in conjunction with the appended claims.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps.

Applicant has discovered that the ease and effectiveness of connecting a spinal fixation device is greatly enhanced by using a unique morse taper locking fit between a pedicle screw and a C-clamp, wherein the pedicle screw is inserted into the bone of the spine and the remainder of the device is later attached to the pedicle screw via the morse taper locking fit. The locking fit may alternatively comprise any suitable taper lock, whether the taper is a true morse taper or some other taper. Applicant has thus conceived of a low profile spinal fixation device that utilizes a taper locking fit, which provides increased strength at the attachment site between the pedicle screw and C-clamp, and also increases the overall efficiency of surgically implanting the spinal fixation device. An illustrative design concept includes pedicle screws, longitudinal rods, stem clamps, and C-clamps for immobilizing and fixing at least one vertebra of the spine to thereby allow fusion of the bone.

Figure 1:
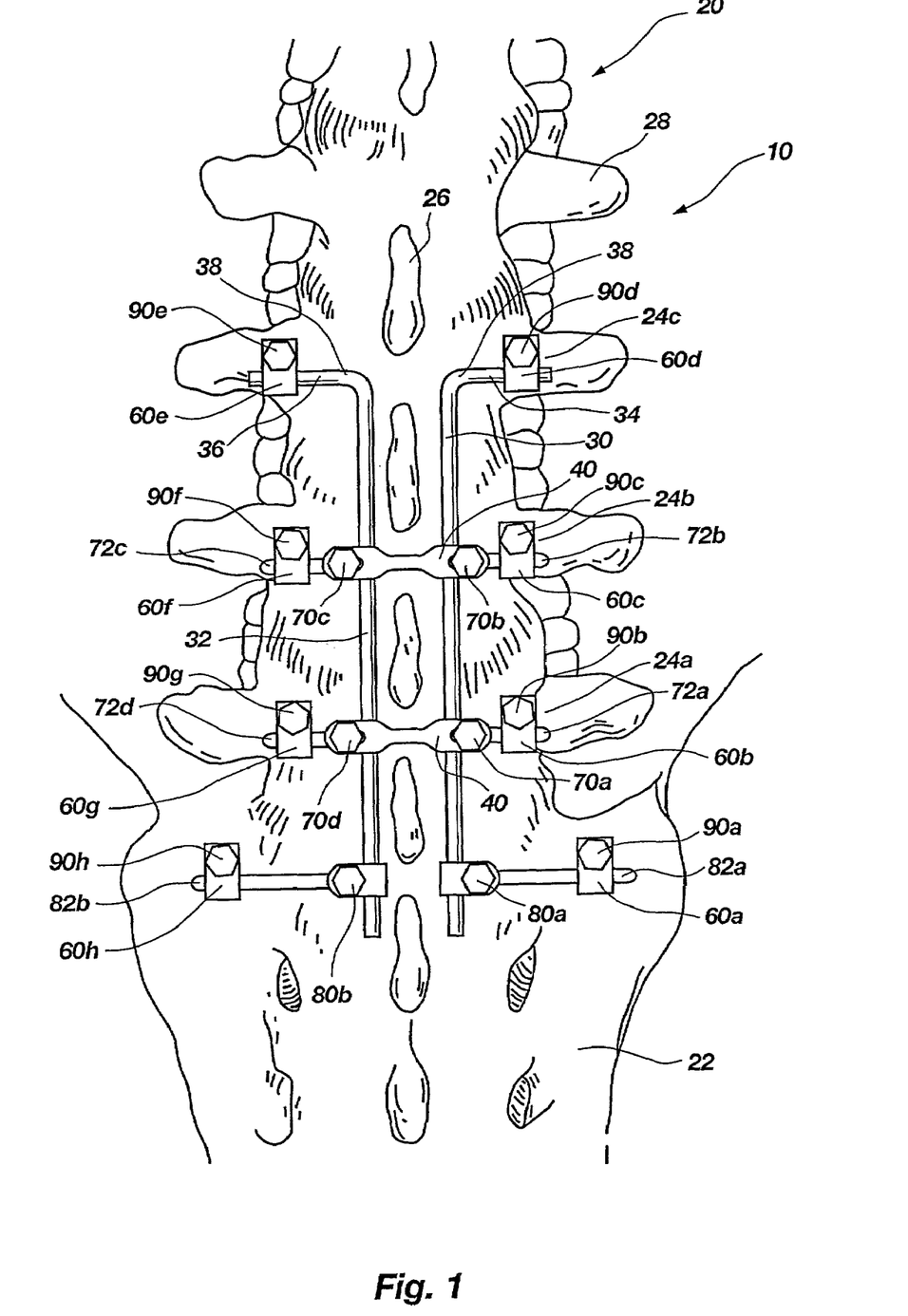
FIG. 1 is a plan view of a spinal fixation device made in accordance with the principles of the present invention.

Referring now to FIG. 1, there is shown a plan view of the spinal fixation device 10, also referred to herein as a bone interconnecting system, fully constructed and attached to the lumbar spinal region 20, just above the sacrum 22. The device 10 includes two longitudinal rods 30, 32 placed substantially parallel to the spinous process 26 and attached to a plurality of vertebrae 24a-24c, pedicle screws 50, C-clamps 60 with a corresponding fastener, stem clamps 70 with a corresponding fastener and cross-link plates 40.

More specifically, pedicle screws 50 (not shown in FIG. 1), which reside beneath set screws 90a-90h, and are first mounted to the pedicle region of the spine, wherein the device 10 is attached to the spine via interaction with the pedicle screws 50. Reference to the longitudinal rods 30, 32 will now be made, but it should be noted that each longitudinal rod 30 and 32 is substantially equivalent, and therefore reference will be made to one longitudinal rod 30, unless otherwise stated. Each longitudinal rod 30 has a substantially orthogonal bend 38 located between each end of the longitudinal rod 30 forming a side arm 34 or 36, which serves as an anchoring site for attaching one end of the longitudinal rod 30 to the spine via a C-clamp 60d, 60e and a pedicle screw 50. The side arm 34 constitutes an upper terminal portion of the longitudinal rod 30, and constitutes about twenty (20%) to about fifty (50%) percent of the total length of said longitudinal rod 30 depending upon the number of vertebrae 24 to be fixed or immobilized. It will be appreciated by those skilled in the art that various lengths of longitudinal rods 30, 32 may be utilized depending upon the number of vertebrae that are to be fused and each variation is intended to fall within the scope of the present invention. Similarly, one skilled in the art will appreciate that side arms 34, 36 may be located on the longitudinal rods 30, 32 at any distance depending upon the fixation needs of the vertebrae. It should be noted that other styles of longitudinal rods 30, 32, which are available or which may become available, may also be utilized and are intended to fall within the scope of the present invention.

Stem clamps 70a-70d may be added to longitudinal rods 30, 32 to provide additional sites for attaching the longitudinal rods 30, 32 to the bone using the previously inserted pedicle screws 50 as anchors. Stem clamps 70a-70d, 80a-80b comprise stems 72a-72d, 82a-82b, which vary in length depending upon the relative placement of the stem clamp 70, 80 on the spine. Additionally, each stem 72a-72d, 82a-82b has a diameter that may be identical to the diameter of the longitudinal rods 30, 32, such that one C-clamp may be selectively attached to either the longitudinal rods 30, 32 or any of the stems 72a-72d, 82a-82b of said stem clamps 70a-70d, 80a-80b as needed. As illustrated in FIG. 1, the longer stems 82a-82b, which extend laterally in relation to the longitudinal rods 30, 32, may be used for attaching the longitudinal rods 30, 32 to the lower lumbar region 20 or the sacral region 22 of the spine. Whereas the shorter stems 72a-72d, which do not extend as far as the longer stems 82a-82b, may be used for attaching said longitudinal rods 30, 32 to other regions of the spine where the longer length is unnecessary.

Prior to the insertion and subsequent tightening of a fastener 100 into a through-passage 73 (shown most clearly in FIG. 3) of the stem clamp 70, a cross-link plate 40 may be used to interconnect two longitudinal rods 30, 32 to increase the rigidity and strength of the device 10. As illustrated in FIG. 1, the cross-link plate 40 comprises a first end and a second end, each of which has an eyelet formed therethrough to allow the fastener 100 to pass through the eyelet into the through-passage 73 of the stem clamp 70, thus providing a mode of attachment. Other devices for interconnecting and stabilizing the longitudinal rods 30, 32 or that provide the same or similar functions as the cross-link plate 40 described herein may also be utilized and are intended to fall within the scope of the present invention.

C-clamps 60a-60h provide a mode for fixing and attaching the longitudinal rods 30, 32 and the stems 72a-72d, 82a-82b to the previously mounted pedicle screws 50 via a clamping action, wherein the C-clamps 60a-60h clamp and secure said longitudinal rods 30, 32 and said stems 72a-72d, 82a-82b.

The longitudinal rods 30, 32, as well as the other component parts of the device 10, may be manufactured from biocompatible materials, such as titanium, which exhibits less image interference (scatter) on a CT scan, because of the infinite capability to place pedicle screws 50 in any orientation without the necessity of bending the longitudinal rods 30, 32. It will be appreciated by those skilled in the art that other biocompatible materials may be utilized in manufacturing of the component parts of the device 10 and fall within the scope of the present invention.

As disclosed herein, a spinal fixation structure may be a longitudinal rod 30, or some other elongate structure such as a spinal plate or a spinal cage assembly (not shown) that is known to those skilled in the art, connected by C-clamps 60, or other connecting members. Stem clamps 70 may also be a part of the spinal fixation structure. It will be appreciated that the spinal fixation structure may be as described above or may be any combination of those structures described above and each is intended to fall within the scope of the present invention.

It will be appreciated that the structure and apparatus disclosed herein as a longitudinal rod 30, or some other elongate structure connected by C-clamps 60, or other connecting members, is merely one example of a spinal fixation structure, or a means for intercoupling the elongate support member with the connecting member, and it should be appreciated that any structure, apparatus or system for connecting the elongate support member with the connecting member, which performs functions the same as, or equivalent to, those disclosed herein are intended to fall within the scope of a means for intercoupling the elongate support member with the connecting member, including those structures, apparatus or systems for intercoupling the elongate support member with the connecting member, which are presently known, or which may become available in the future. Anything which functions the same as, or equivalently to, a means for intercoupling the elongate support member with the connecting member falls within the scope of this element.

Additionally, it will be appreciated an elongate support member may be a longitudinal rod 30, a spinal plate or even a cage assembly (not shown). Each of the elongate support members has the ability to be attached to at least two vertebrae of the spine, thus interconnecting two or more vertebrae. Therefore, an elongate support member is not the same as the above described spinal fixation structure as no clamp is present in the elongate support member as there is in the spinal fixation structure.

Figure 2:
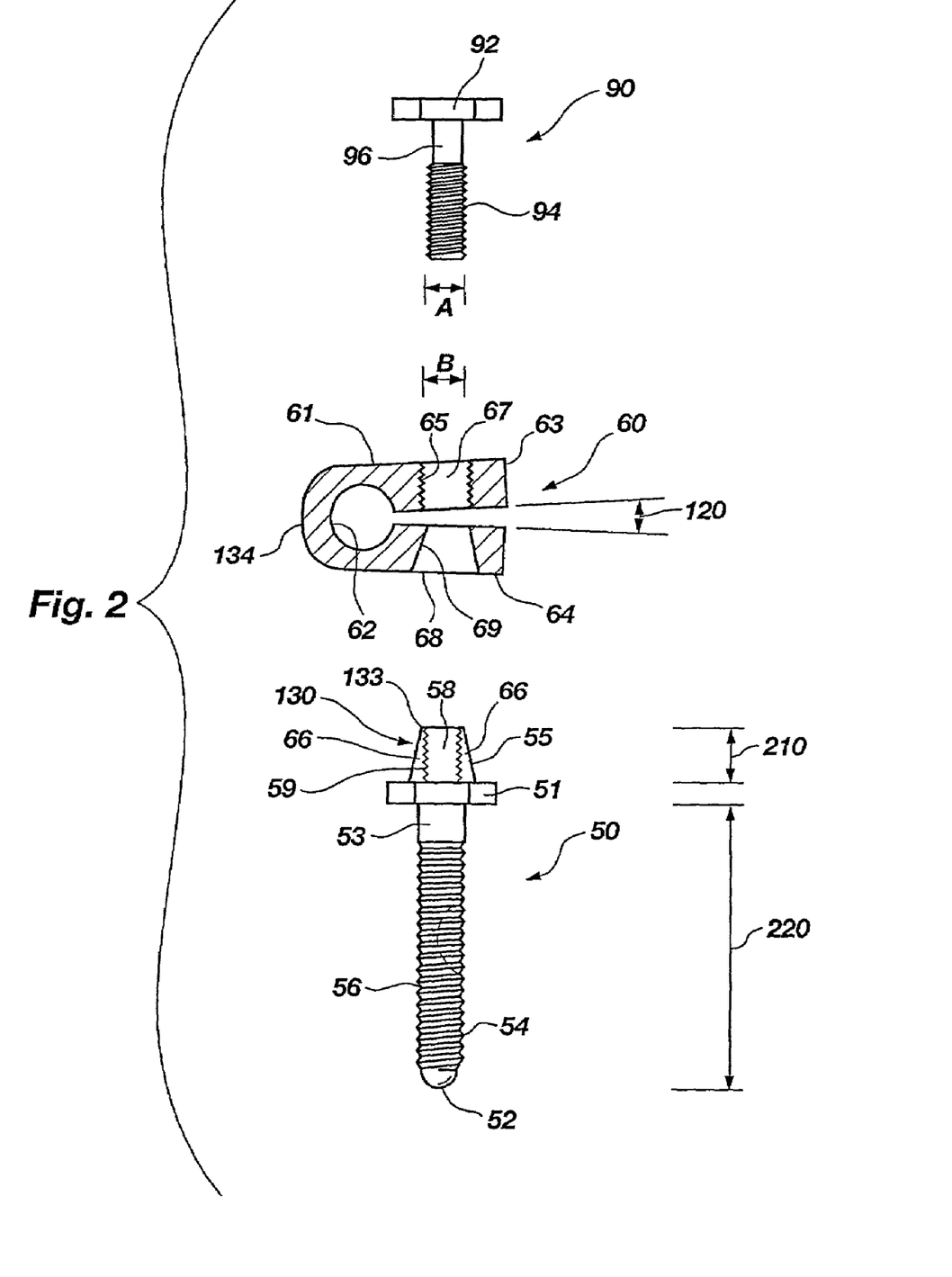
FIG. 2 is an exploded side view showing the relationship between a set screw, a C-clamp taken in cross section, and a pedicle screw, made in accordance with the principles of the present invention.

Referring now to FIG. 2, wherein an exploded side view of a set screw 90, a C-clamp 60 (shown in a side cross-section), and a pedicle screw 50 are shown in relation to one another. Specifically, the set screw 90, the C-clamp 60 and the pedicle screw 50 may be interconnected to form a locking mechanism that is capable of locking the longitudinal rod 30 and the pedicle screw 50 in place on the spine. The set screw 90, sometimes referred to herein as a fastener, comprises a head portion 92, and a shaft portion 96. Those skilled in the art will appreciate that the time for the surgical procedure may be reduced by the use of similar sized component parts that may be tightened and located with the same sized tools. For example, the head portion 92 may be hexagonal in shape and configured and dimensioned to fit the same sized tool as a similar mid-collar 51 portion of the pedicle screw 50. Other shapes known, polygonal or otherwise, or used by one of skill in the art may be utilized in place of the hexagonal head portion 92 and is intended to fall within the scope of the present invention. The shaft 96 of the set screw 90 comprises male threads 94 which are configured and dimensioned to mate with the opposite female threads 59 of a recess 58 formed in the pedicle screw 50.

Additionally, the set screw 90 has a base width, which is represented by the distance A, less than the corresponding opening of the threaded through-passage 67 of the C-clamp 60, which distance is represented by B, such that A is smaller than B. Additionally, when the upper portion 63 and the lower portion 64 are aligned the set screw 90 is capable of passing through the upper threaded portion 67 of said C-clamp 60 without obstruction or interference allowing the male threads 94 to threadedly engage the female threads 59 of said pedicle screw 50. It should be noted that any structure or fastener, which performs functions the same as or similar to the set screw 90, is intended to fall within the scope of the present invention.

The C-clamp 60 is characterized by a body 61 with an upper portion 63 and a lower portion 64. The upper portion 63 comprises a through-passage 67 that has female threads 65 for connecting the C-clamp 60 to a distractor 120 or another instrument for holding and placing the C-clamp 60 (shown most clearly in FIG. 8). The distractor 120 is used to release the locking fit, as discussed more fully below, that occurs between the pedicle screw 50 and the C-clamp 60 after being attached by way of a morse taper locking fit. The distractor 120 may be screwed into the upper portion 63 until the bottom 122 of the distractor 120 (shown most clearly in FIG. 5A) strikes and displaces the pedicle screw 50, releasing the locking fit.

As further discussed above, the width of the through-passage 67, represented by distance B, is greater than the width, represented by distance A, of the set screw 90. The lower portion 64 comprises a through-passage 68 with sidewalls that form an internal female-taper 69, which tapers outwardly in a proximal-to-distal direction. The upper portion 63 and the lower portion 64 share a concave sidewall 134 which defines a lateral through-passage 62 wherein the longitudinal rods 30, 32 and the stems 72, 82 of the stem clamps 70, 80 may be clamped and locked. The clamping occurs when the set screw 90 is inserted through the upper portion 63 of the C-clamp 60 and threadedly engaged within the recess 58 of the pedicle screw 50 after the morse taper interlock fit is initiated between the pedicle screw 50 and the C-clamp 60. Additionally, the upper portion 63 and the lower portion 64 have a limited degree of resiliency and are offset by an angle 120, wherein the angle 120, being greater than zero degrees, allows the longitudinal rods 30, 32 and the stems 72, 82 to be positioned within the lateral through-passage 62 and subsequently clamped when a compression force is applied to the C-clamp 60. The C-clamp 60 has a locked and an unlocked position, wherein the C-clamp 60 remains in the unlocked position and has a limited degree of resiliency in maintaining its original shape to thereby enable the upper portion 63 of said C-clamp 60 to be compressed toward the lower portion 64 of said C-clamp 60 and into the locked position. The compression force may be brought about by the insertion of the set screw 90 through the C-clamp 60 and into the recess 58 of the pedicle screw 50, and then subsequent tightening of the set screw 90 maintains the C-clamp 60 in the locked position. The compression force clamps the longitudinal rods 30, 32 and stems 72, 82 locking them in place.

It will be appreciated that the structure and apparatus disclosed herein is merely one example of a connecting member, or a means for connecting the elongate support member to the fastening member, and it should be appreciated that any structure, apparatus or system for connecting the elongate support member to the fastening member, which performs functions the same as, or equivalent to, those disclosed herein are intended to fall within the scope of a means for connecting the elongate support member to the fastening member, including those structures, apparatus or systems for connecting the elongate support member to the fastening member, which are presently known, or which may become available in the future. Anything which functions the same as, or equivalently to, a means for connecting the elongate support member to the fastening member falls within the scope of this element.

The pedicle screw 50, sometimes referred to herein as a fastening member, is configured and dimensioned to penetrate and attach to a bone and comprises a head, generally referred to at 130, containing a male-taper 55, a mid-collar 51, a neck 53 and a shaft 54. The male-tapered head 55 tapers outwardly in proximal-to-distal direction and is configured and dimensioned to matingly engage the female-taper 69 located within the through-passage 68 of the C-clamp 60 in static, frictional engagement creating a morse taper locking fit. The male-tapered head 55 generally contains two sides. The first side is inserted into the bottom opening of the female-tapered first through-passage 68 and the second side protrudes from the bottom of the opening of the female-tapered first through-passage 68 when the pedicle screw 50 is connected to the C-clamp 60. The male-tapered head 55 also contains a recess 58 formed therein, the male-tapered head contains internal sidewalls defining said recess 58. In the present embodiment, said recess 58 comprises a threaded interior surface 59. However, it should be noted that the recess 58 may be threaded as illustrated in FIG. 2, or it may not be threaded, and may possibly include other means for engaging the set screw 90 with the recess 58, such as an interference fit or other means known by one skilled in the art. Phantom lines 66 represent the channel formed in the male-tapered head 55. When the pedicle screw 50 and the C-clamp 60 are engaged in a morse taper locking fit, the shaft 96 of the set screw 90 is inserted through the through-passage 67 of the upper portion 63 of said C-clamp 60 and into the threaded recess 58, wherein the set screw 90 is threadedly engaged with the pedicle screw 50 bringing the upper portion 63 and the lower portion 64 together and clamping the longitudinal rods 30, 32 or the stems 72, 82. It should be noted that the upper portion 63 and the lower portion 64 do not contact one another when in the locked or clamped position. The diameter of the longitudinal rod 30 or the stems 72, 82 have large enough dimensions such that the gripping space 62 clamps around the longitudinal rod 30 or the stems 72, 82, but does not allow the upper portion 63 and lower portion 64 to contact one another.

The pedicle screw 50 may be viewed as having a first side 210 and a second side 220 with a mid collar 51 separating the first side 210 from the second side 220, the second side 220 having threads for attaching the fastening member to the bone. Illustratively, the length of the second side 220 of the pedicle screw 50 may be between the range of two to ten times the length of the first side 210. Specifically, the length of the second side 220 may be between the range of two to six times the length of the first side 210. More specifically, the length of the second side 220 may be between the range of two to three times the length of the first side 210. The mid-collar 51 is configured and dimensioned in a hexagonal shape, which is the same size as the set screw's 90 hexagonal head 92 such that the same instrumentation may be used to tighten both pieces. The shaft 54 of the pedicle screw 50 comprises threads 56 for insertion into the bone and a blunt tip 52. While the neck 53, as illustrated, does not contain threads, it should be noted that the neck 53 may be threaded such that there is no distinction between the shaft 54 and the neck 53.

Figure 2A:
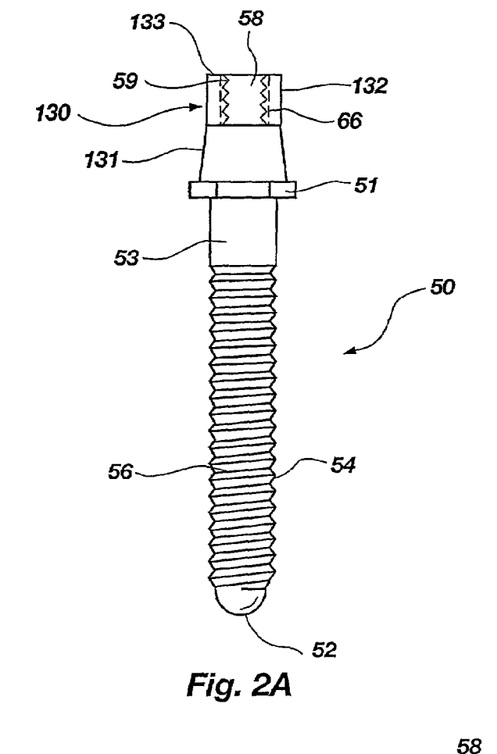
FIG. 2A is a side view of a second embodiment of a pedicle screw made in accordance with the principles of the present invention.

A second embodiment of the pedicle screw 50 is illustrated in FIG. 2A, with the same reference numerals referring to the same or similar structures as illustrated in FIG. 2, with only the differences being directly mentioned. In this embodiment, the head 130 comprises a first head portion and a second head portion. Further, the second head portion may be a tapered portion 131 of the pedicle screw 50 as illustrated. The tapered portion 131 is not illustrated as the terminal end 133 of the head 130, but is nevertheless part of the head 130 structure. In this embodiment, the terminal end 133 of the head 130, which is the first head portion, is formed as a cylinder, generally referred to at 132. The cylindrical portion 132 is formed on the top of the tapered portion 131, thus the overall structure of the head 130 includes a terminal cylindrical portion 132 and a tapered portion 131.

Figure 2B:
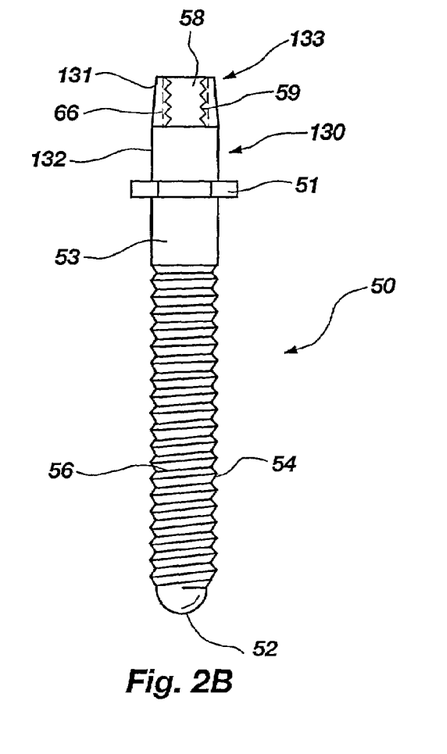
FIG. 2B is a side view of a third embodiment of a pedicle screw made in accordance with the principles of the present invention.

FIG. 2B is essentially the same as FIG. 2A, however, FIG. 2B illustrates a third embodiment of the pedicle screw 50 and the head 130. As with the embodiment of FIG. 2A, the head 130 comprises a first head portion and a second head portion, with the exception being the first head portion is formed as a tapered portion 131, and the second head portion being formed as a cylindrical portion 132. The cylindrical portion 132, instead of being located on top of the tapered portion 131 as in FIG. 2A, is located beneath the tapered portion 131. Thus, in the third embodiment of the pedicle screw 50, the tapered portion 131 defines the terminal end 133.

The embodiments represented in FIGS. 2A and 2B may be modified to contain a first head portion and a second head portion that are both configured and dimensioned as tapered portions (not shown in the figures). Alternatively, the first head portion and the second head portion may both be configured and dimensioned substantially as cylindrical portions (not shown in the figures). Other modifications may be made to the pedicle screw 50 similar to those disclosed herein and said modifications are intended to fall within the scope of the present invention.

Figure 2C:
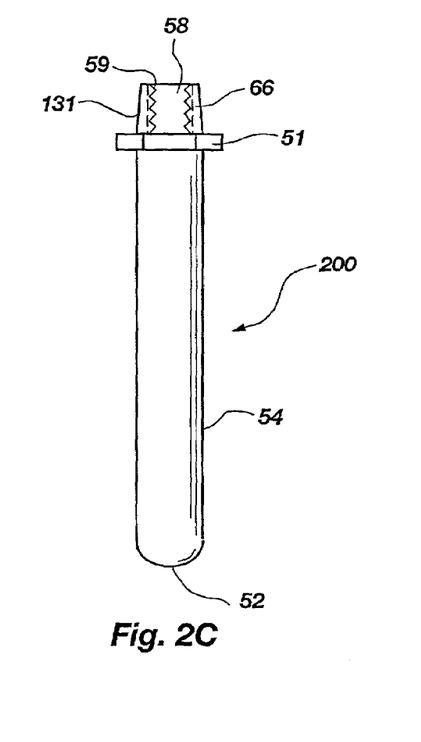
FIG. 2C is a side view of a bone pine having a male-tapered external portion made in accordance with the principles of the present invention.

FIG. 2C illustrates another embodiment of the present invention utilizes a pin 200, another type of fastening member, in conjunction with a cement or an epoxy (not shown in the figures) to attach the device 10 to the spinal column, essentially replacing the pedicle screw. The pin 200 is similar in structure and also has a similar function as the pedicle screw 50. It should be noted that the pin 200 utilizes the same tapered portion 131, a similar recess 58 for receiving a set screw 90, and a shank 54 similar to the pedicle screw embodiments, but the shank 54 does not contain threads 56. Attachment may be accomplished through pre-drilling holes in the spinal bone tissue and using the aforementioned bone cement or epoxy to secure the pin 200 to the bone. The pin 200 structure also utilizes a morse tapered portion 131 for intercoupling with the female-tapered through passage 68 of the C-clamp 60 in a morse taper interlock fit. As will be appreciated by those skilled in the art, the bone pin 200 has been used in conjunction with a cage assembly (not shown) and the features described herein may be used effectively on such an assembly.

It will be appreciated that the structures and apparatuses disclosed herein are merely examples of a means for attaching a spinal fixation device to a bone, and it should be appreciated that any structure, apparatus or system for penetrating and attaching a spinal fixation device to the bone, which performs functions the same as, or equivalent to those disclosed herein, are intended to fall within the scope of a means for attaching a spinal fixation device to the bone, including those structures, apparatus or systems for penetrating and attaching to a bone which are presently known, or which may become available in the future. Anything which functions the same as, or equivalently to, a means for attaching a spinal fixation device to the bone falls within the scope of this element.

Referring back to FIG. 2, the engagement between the male-tapered head 55 and the female-tapered through-passage 68 creates a morse taper locking fit, which provides additional strength and support to the device 10 as a whole. The morse taper locking fit is such that when engaged, the pedicle screw 50 and the C-clamp 60 cannot be separated without the aid of an instrument or a distractor 120 (shown most clearly in FIG. 5A).

The morse taper increases the ease of attachment of the C-clamp 60 onto the pedicle screw 50 as compared to a cylindrical head and provides increased strength over a polyaxial screw. Additionally, the construct of the set screw 90, the C-clamp 60 and the pedicle screw 50 creates a very low profile device so that less of the internal structures of the patient are contacted, which results in increased comfort for the patient. The morse taper locking fit also reduces the number of individual pieces and component parts that are required for the surgeon to attach during an operation, and results in far less bulk than other devices used in the industry. Another key feature created by the morse taper locking fit is the decrease in motion and wobble of the device 10 during installation and insertion because the morse taper locking fit holds the device 10 sturdily in place.

Figure 3:
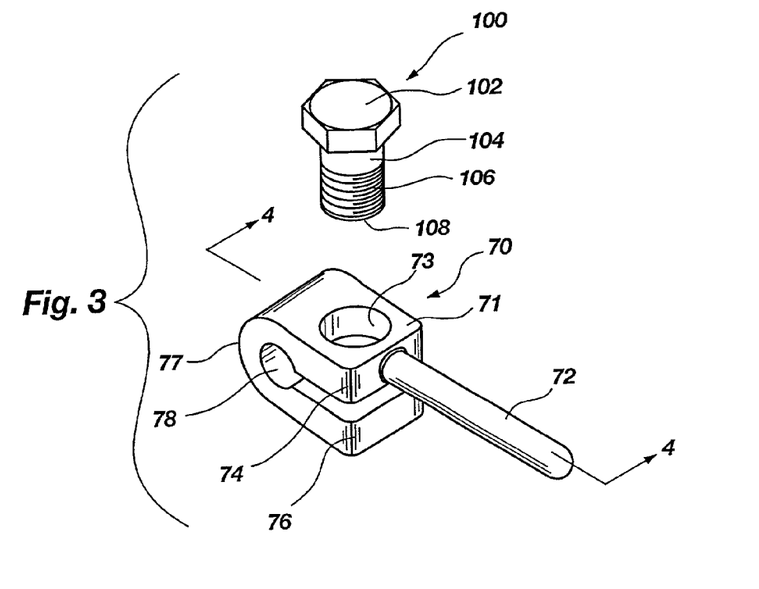
FIG. 3 is an exploded, perspective view of a stem clamp and a fastener made in accordance with the principles of the present invention.
Figure 4:
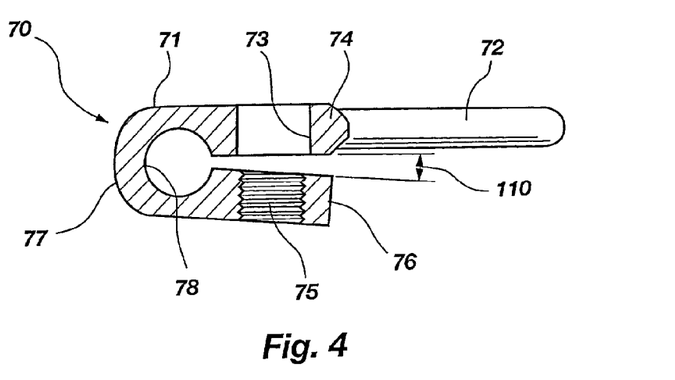
FIG. 4 is a side, cross-sectional view taken along the line 4-4 of the stem clamp of FIG. 3.

Referring now to FIG. 3 and FIG. 4, in FIG. 3 is shown a stem clamp 70 in a perspective view along with a fastener 100, and in FIG. 4 is shown a side cross-sectional view taken along the line 4-4 of the stem clamp 70. The fastener 100 comprises a head 102, a neck 104 and a shaft 108. The head 102 may be hexagonally shaped and may be further configured and dimensioned to fit the same sized instrument or tool as the hexagonal head 92 of the set screw and the mid-collar 51 of the pedicle screw 50. It will be appreciated by those skilled in the art that the hexagonal shape of any of the aforementioned structures may be modified to any polygonal or circular shape, and such modification falls within the scope of the present invention. The neck 104 is unthreaded, while the shaft 108 comprises threads 106 for threadedly engaging the lower portion 76 of the stem clamp 70. It should be noted that the neck 104 may also be threaded such that there is no distinction between the shaft 108 and the neck 104.

The stem clamp 70, sometimes referred to herein as a stem member, comprises a body 71 with an upper portion 74 and a lower portion 76, wherein the upper portion 74 contains a through-passage 73 that is non-threaded and said upper portion 74 further being structurally in contact with the stem 72, sometimes referred to herein as a stem portion. The lower portion 76 contains a threaded through-passage 75 for threadedly engaging the threaded shaft 108 of the fastener 100 thereby depressing the upper portion 74 and bringing said upper 74 portion into contact with the lower portion 76 and providing a clamping action for attachment to the longitudinal rods 30, 32. The stem clamp 70 further comprises a concave sidewall 77 that defines a lateral through-passage 78 wherein the longitudinal rod 30 may pass prior to the clamping action. The upper portion 74 and the lower portion 76 have a limited degree of resiliency and have an angle 110, wherein said angle 110 is greater than zero degrees.

Those skilled in the art can arrive at modifications and arrangements of the illustrated structure which perform functions equivalent to the stem clamp 70, 80 disclosed in FIGS. 3-4, and such modifications and arrangements, both those which can be devised at present and those which will be devised in the future by those skilled in the pertinent art, are intended to fall within the scope of the present invention.

Figure 5:
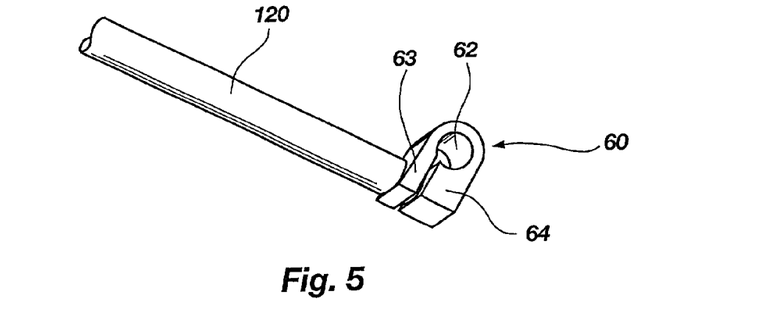
FIG. 5 is a side view of another embodiment of the C-clamp shown in FIG. 2, with a distractor device made in accordance with the principles of the present invention.

Referring now to FIG. 5, wherein a side view of a second embodiment of a C-clamp 60 engaged with a distractor 120 is illustrated. In the second embodiment of the C-clamp 60, the lower portion 64 of the C-clamp 60, which embodiment may also be utilized in the stem clamp 70, is larger in size than the upper portion 63. Illustratively, the lower portion 64 is at least twice the size and thickness of the upper portion 63. It should be noted that upper portion 63 and lower portion 64 may be configured and dimensioned in a number of differing sizes, all of which are intended to fall within the scope of the present invention, and the embodiments herein are illustrative of the differing sizes that may be implemented by one of skill in the art. The upper portion 63 and lower portion 64 define the lateral through-passage 62 discussed above.

Figure 5A:
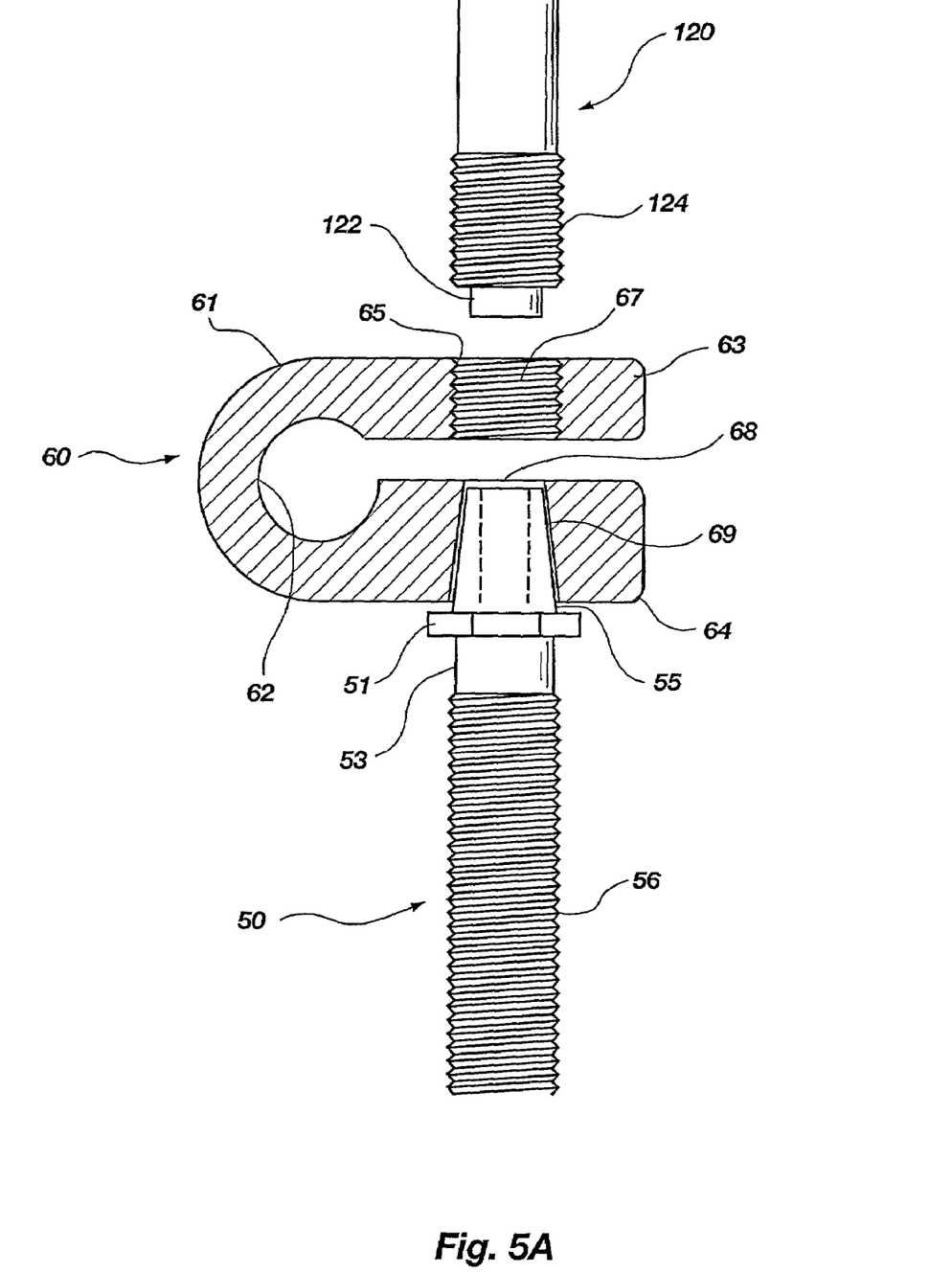
FIG. 5A is an enlarged side view of the distractor device as it is being inserted into the C-clamp for disengaging the morse taper locking fit between the C-clamp and the pedicle screw.

Referring to FIG. 5A, the distractor device 120 may be used to release the morse taper locking fit that occurs between the pedicle screw 50 and the C-clamp 60. The distractor 120 comprises male threads 124 for threadedly engaging the female threads 65 of the threaded through-passage 67. The distractor 120 may be screwed into the upper portion 63 of the C-clamp 60 until the bottom 122 of the distractor 120 strikes and displaces the pedicle screw 50, releasing the morse taper locking fit. FIG. 5 shows the engagement between the C-clamp 60 and the distractor 120, while FIG. 5A illustrates the distractor 120 prior to disengaging the morse taper locking fit between the pedicle screw 50 and the C-clamp 60. It will be appreciated that the structure and apparatus disclosed herein is merely one example of a means for disengaging the locking fit between the C-clamp 60 and the pedicle screw 50, and it should be appreciated that any structure, apparatus or system for disengaging the locking fit, which performs functions the same as, or equivalent to, those disclosed herein are intended to fall within the scope of a means for disengaging, including those structures, apparatus or systems for disengaging the locking fit which are presently known, or which may become available in the future. Anything which functions the same as, or equivalently to, a means for disengaging falls within the scope of the present invention.

FIG. 6 through FIG. 12 are selected figures illustrating the sequential steps for implantation of the device 10 onto the spine, and reference to FIG. 6 through FIG. 12 should therefore be made sequentially.

Figure 6:
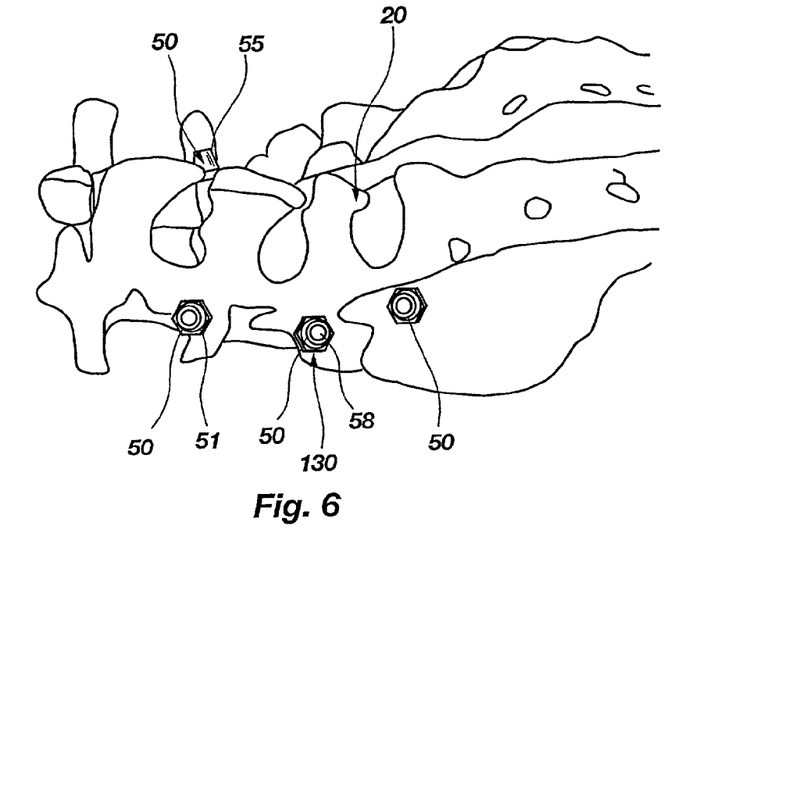
FIG. 6 is a perspective view of a plurality of pedicle screws inserted into the spine in accordance with the principles of the present invention.

FIG. 6 is a perspective view of the lumbar region 20 of the spine with pedicle screws 50 inserted therein. Insertion of the pedicle screws 50 into the vertebrae of the spine wherein said pedicle screws 50 are placed at a preselected location of the spine, such as the pedicle region, which insertion causes said pedicle screws 50 to be anchored to the bone. The shaft 54 of each pedicle screw 50 is driven into the bone by a screw-driving tool 150 (shown most clearly in FIG. 12) as the screw-driving tool grips the hexagonal mid-collar 51 and screws the pedicle screw 50 into the bone leaving the head 130 exposed. The male-tapered end 55 of said pedicle screw 50 is left exposed, as shown, to thereby allow subsequent connection of the device 10 to the pedicle screw 50. More particularly, the longitudinal rod 30, the stem clamp 70, the C-clamp 60, and the cross-link plate 40 may be attached to the pedicle screw 50 via their respective modes of attachment as discussed more fully above.

Figure 7:
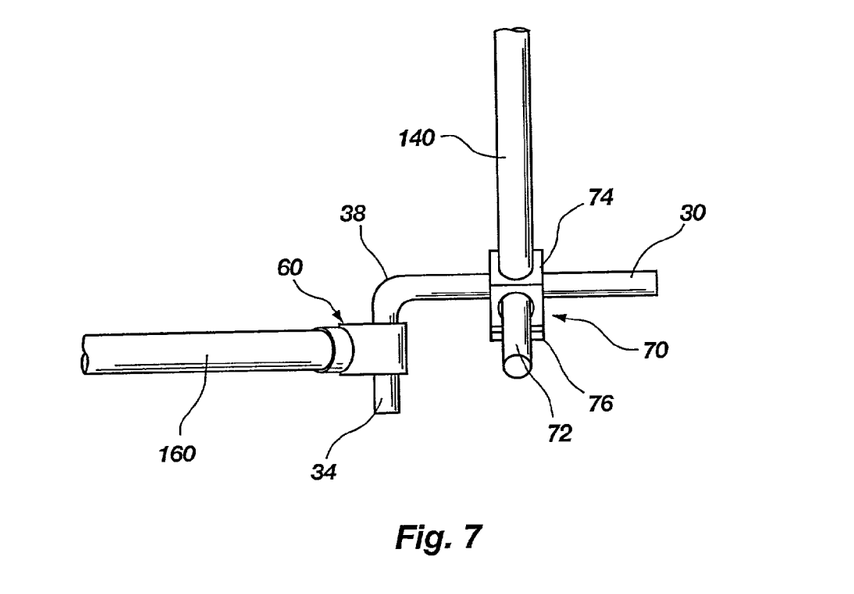
FIG. 7 is a side view of a longitudinal rod with a C-clamp and a stem clamp slidably disposed upon said longitudinal rod made in accordance with the principles of the present invention.

After inserting the pedicle screws 50, a longitudinal rod 30 is selected and obtained for connecting a C-clamp 60 and at least one stem clamp 70 as shown in FIG. 7. Also illustrated in FIG. 7 is a device 140 for holding and manipulating the stem clamp 70 and a device 160 for holding and manipulating the C-clamp 60 during an operation. Likewise, the longitudinal rod 30 having an orthogonal bend 38 is illustrated in relation to the other component parts prior to insertion of the construct onto the bone of the spine.

Figure 8:
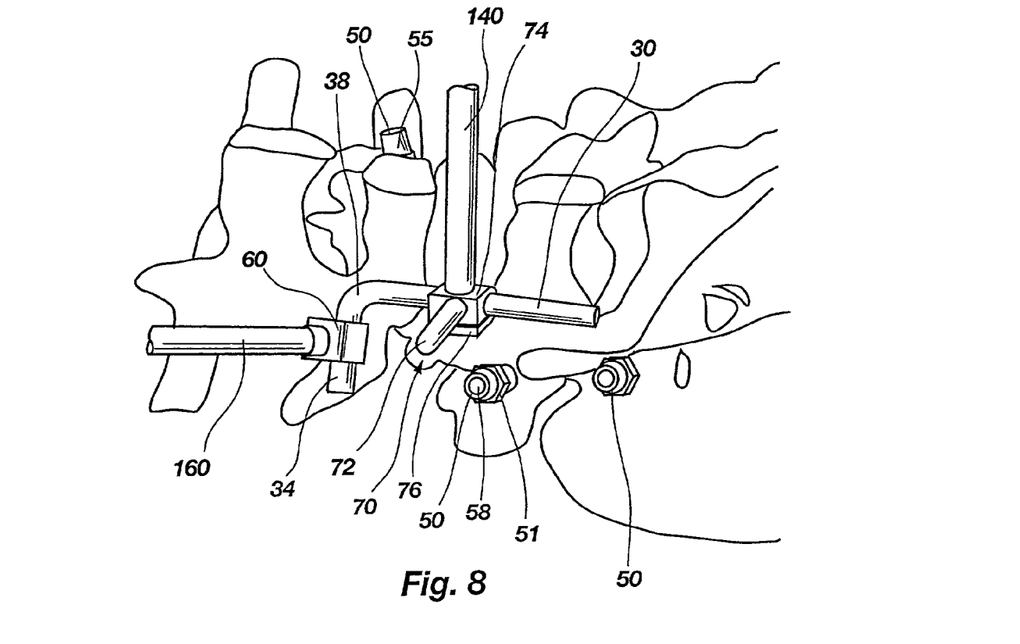
FIG. 8 is a perspective view, similar to FIGS. 6 and 7 combined, wherein the device, including a longitudinal rod, a C-clamp and a stem clamp, is shown in relation to the spine and attached pedicle screws in accordance with the principles of the present invention.

Referring now to FIG. 8, wherein the construct of FIG. 7 has been placed near the spine for connecting the longitudinal rod 30 to a pedicle screw 50 via a C-clamp 60 as shown. Implantation of the longitudinal rod 30 onto the spine occurs by first, connecting the C-clamp 60, located on side arm 34, to the pedicle screw 50 as described more fully above. In short, the female-taper 69 of the lower portion 64 of the C-clamp 60 mates with the male-taper 55 of the pedicle screw 50 (shown most clearly in FIG. 2) to form a morse taper locking fit, thereafter the set screw 90 is positioned through the threaded through-passage 67 of the C-clamp 60 and into the threaded recess 58 of the pedicle screw 50. FIG. 8 is taken at the moment in time just after inserting the male-tapered portion 55 of the pedicle screw 50 into the female-tapered portion 69 of the C-clamp 60, but prior to insertion of the set screw 90. The device 160, which holds the C-clamp, will remain in place until the morse taper locking fit has been accomplished, which allows for subsequent insertion of the set screw 90 into the threaded opening 67 where the device 160 was previously located. Also shown in this figure are the various component parts of the pedicle screw 50, the C-clamp 60 and the stem clamp 70 in relation to each other and the spine.

Figure 9:
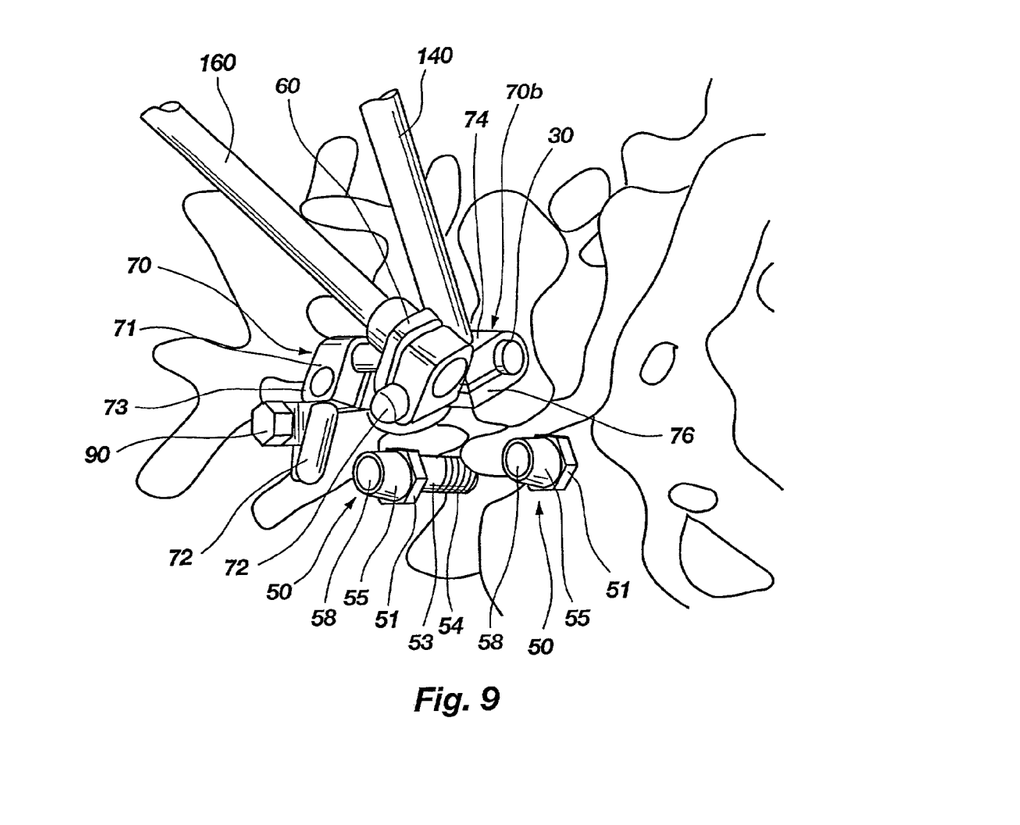
FIG. 9 is a perspective view of the device wherein an additional stem clamp is added to the longitudinal rod prior to attaching the stems to the pedicle screws in accordance with the principles of the present invention.

Placement of a second stem clamp 70b onto the longitudinal rod 30 is illustrated in FIG. 9. As illustrated, the set screw 90 has been inserted and tightened and the process of placing a second stem clamp 70b, which is accompanied by a C-clamp interconnected to the stem 72 of said stem clamp 70, has just been accomplished using instrumentation devices 160 and 140.

Figure 10:
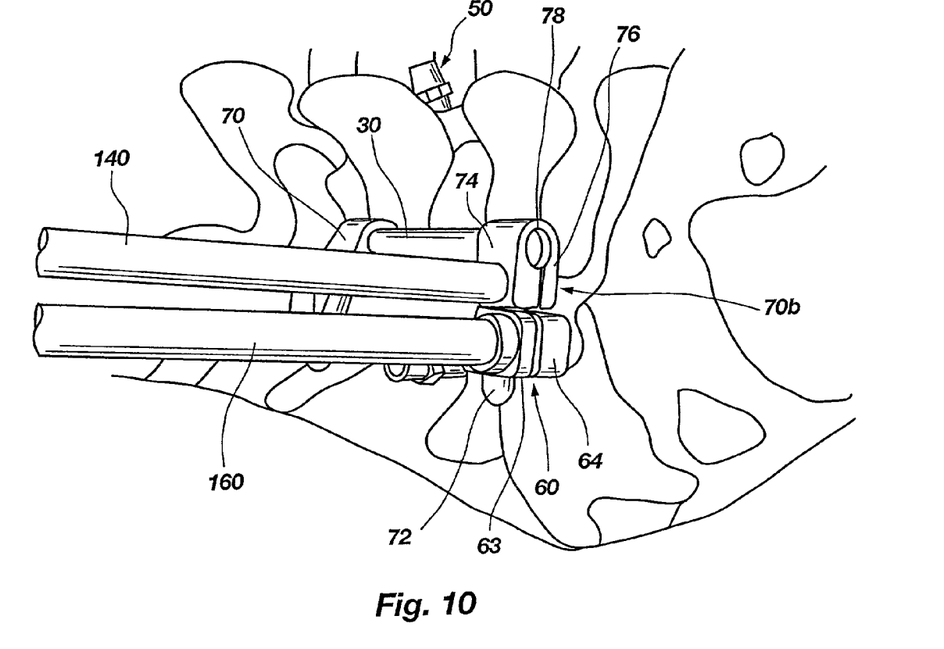
FIG. 10 is a perspective view of the device wherein a stem clamp is attached to a pedicle screw via a C-clamp in accordance with the principles of the present invention.

After the second stem clamp 70b has been located onto the longitudinal rod 30, the second stem clamp 70b is then connected to the pedicle screw 50 via a second C-clamp 60 that is attached to the stem 72, as shown in FIG. 10. The use of instrumentation devices 160 and 140 provide the surgeon with the capability of accurately attaching the C-clamp 60 to the pedicle screw 50. Once the morse taper locking fit has been accomplished between the male-taper 55 of the pedicle screw 50 and the female-taper 69 of the C-clamp 60, the set screw 90 may be inserted and tightened. Thereafter, the device 140 holding the stem clamp 70b may be released and the fastener 100 inserted and tightened providing the necessary clamping action between the stem clamp 70 and the longitudinal rod 30.

Figure 11:
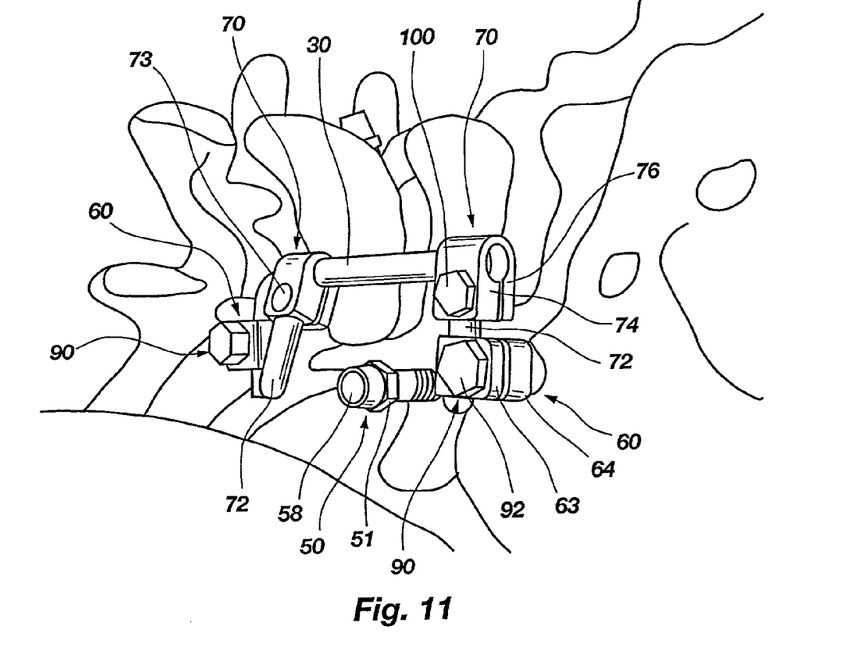
FIG. 11 is a perspective view of the device, similar to FIG. 10, showing the completed attachment of the first stem clamp to the pedicle screw via a C-clamp in accordance with the principles of the present invention.

FIG. 11 illustrates the completed step of inserting the set screw 90 into the pedicle screw 50 securing the C-clamp 60 to the bone. Also shown is the fastener 100 in its fastened position clamping the stem clamp 70 to the longitudinal rod 30. The process described above is repeated until each stem 72 has been connected to a corresponding pedicle screw 50 via the C-clamp 60 and the longitudinal rod 30 is satisfactorily mounted to the spine.

Figure 12:
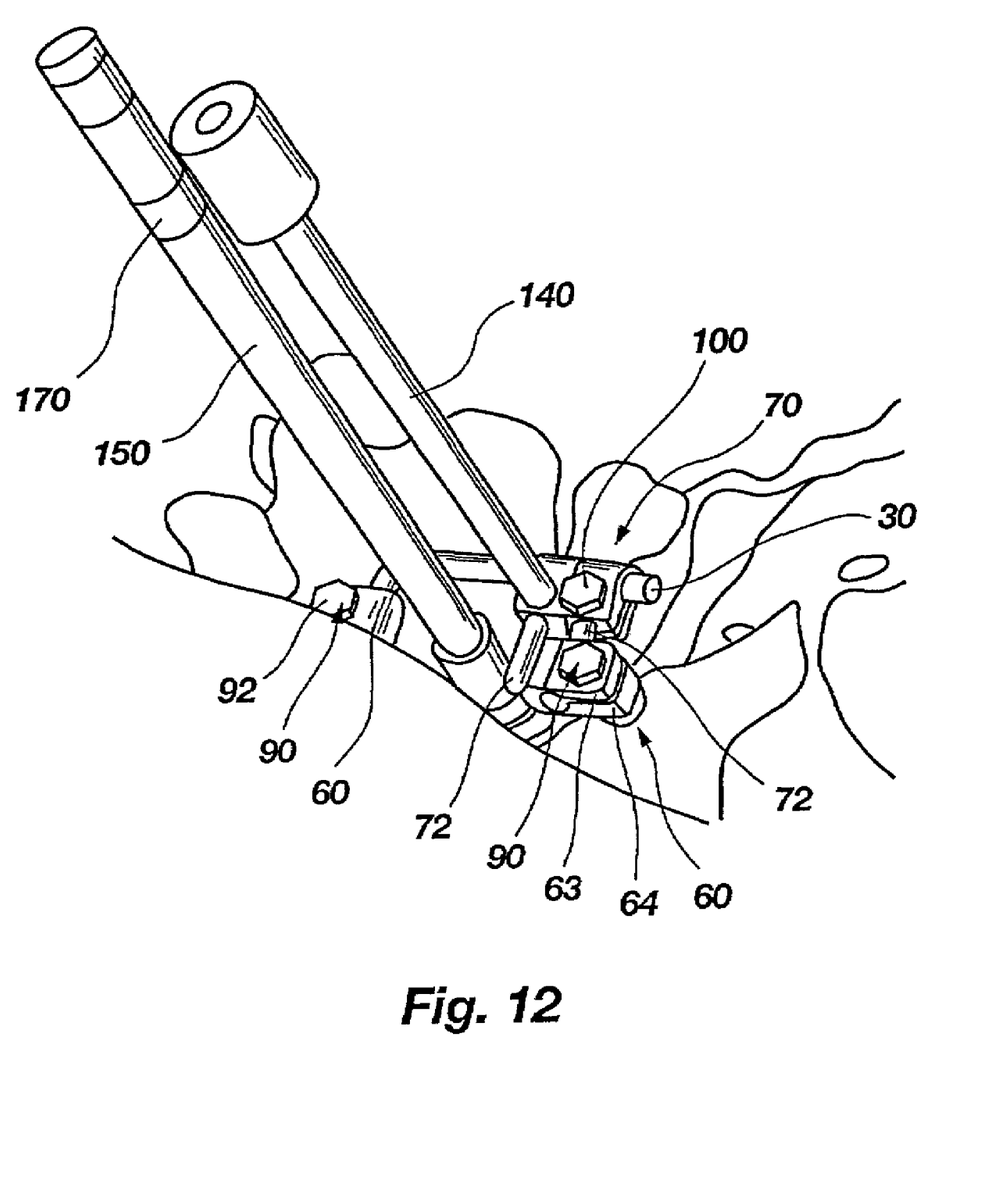
FIG. 12 is a perspective view of the device showing the relative orthogonal placement of the pedicle screw in relation to the stem of the stem clamp in accordance with the principles of the present invention.

Referring now to FIG. 12, once connected to the longitudinal rod 30, the stem clamp 70 is capable of rotating about the axis of said longitudinal rod 30 prior to being clamped. By subsequently connecting the C-clamp 60 to the stem 72 of said stem clamp 70, the C-clamp 60 is capable of rotating along the axis of the stem 72 of said stem clamp 70 prior to being attached to the pedicle screw 50. Thus, an infinite number of angles of attachment may be accommodated by the invention disclosed herein because of the rotational ability of the stem clamp 70 about the longitudinal rod 30 and the C-clamp 60 about the stem 72 of the stem clamp 70.

It is important to emphasize that the versatility of construct 10 is significantly enhanced by the fact that pedicle screws 50 are capable of being directed in any preselected angular orientation into the particular underlying bone structure of the spine. For example, the proper angular orientation of pedicle screws 50d and 50e is achieved by rotating the respective longitudinal rods 30 and 32 to bring side arms 34 and 36 into the desired placement relative to the spine. Correspondingly, C-clamps 60d and 60e are rotated about side arms 34 and 36 respectively, to correctly orient the angular position of bone screws 50d and 50e, respectively, with the spine.

Similarly, C-clamps 60a-60c and 60f-60h are rotatable a full 360 degrees about the respective stems of stem clamps 80a and 80b, and 70a-70d, or rotatable about the side arms 34 and 36 of the respective longitudinal rods 30 and 32, while stem clamps 80a, 80b, and 70a-70d are also rotatable a full 360 degrees about longitudinal rods 30 and 32, respectively. This feature allows the surgeon to have an infinite choice for the angular orientation of the respective pedicle screws 50a-50c and 50f-50h. Thus, each pedicle screw 50, associated with a corresponding stem clamp 70, may be inserted into the bone and aligned at substantially a right-angle with respect to the stem 72 of said corresponding stem clamp 70.

Additionally, instrumentation devices 140 and 150 aid in the aligning process. As illustrated in FIG. 12, the instrumentation devices 140 and 150 are designed such that there is a depth reference gauge for referencing the depth of the intermittent pedicle screws 50, when surgical placement is difficult to see and feel. The depth reference is represented as a darkened band 170 and is located on the screw-driving tool 150. As the pedicle screw 50 is inserted into the bone using said screw-driving tool 150, the depth reference band 170 is moved downward in relation to the screw-driving motion until the top of band 170 is equal to the top of the instrumentation device 140, which device 140 is for holding the stem clamp 70 or a C-clamp 60. When the depth reference band 170 and the top of the device 140, the pedicle screw 50 is at the desired depth, and there is an orthogonal relationship between the pedicle screw 50, the stem clamp 70 and the longitudinal rod 30.

It will be appreciated that the structure and apparatus disclosed herein, in the form of C-clamps 60, stem clamps 70, longitudinal rods 30, 32 and instrumentation devices 140 and 150, is merely one example of a means for aligning the screw member and the stem member to thereby cause said screw member to be positioned in a substantially orthogonal position, and it should be appreciated that any structure, apparatus or system for aligning the pedicle screw 50 and the stem 72 to thereby cause said pedicle screw 50 to be positioned in a substantially orthogonal position with respect to said stem 72 which performs functions the same as, or equivalent to, those disclosed herein are intended to fall within the scope of a means for aligning, including those structures, apparatus or systems for aligning the pedicle screw 50 and the stem 72 which are presently known, or which may become available in the future. Anything which functions the same as, or equivalently to, a means for aligning falls within the scope of this element.

In accordance with the features and combinations described above, one method of spinal fixation includes the steps of:

(a) attaching a plurality of pedicle screws 50 to the bone of the spine, leaving the male-tapered head 55 exposed;

(b) attaching an initial C-clamp 60 and at least one stem clamp 70 to the longitudinal rod 30;

(c) attaching the longitudinal rod 30 to the pedicle screw 50 by first engaging the morse taper locking fit by engaging the female-taper 69 of the through-passage 68 of the C-clamp 60 with the male-taper 55 of the head 130, and then inserting a set screw 90 through the threaded through-passage 67 of the C-clamp 60 and into the threaded recess 58 of the pedicle screw 50; and (d) attaching each stem clamp 70 to the pedicle screw 50 by connecting a C-clamp 60 to each corresponding stem clamp 70, and engaging the morse taper locking fit of said C-clamp 60 and inserting a set screw 90 as described in (c) above, and then inserting a fastener 100 into through-passage 73 of the stem clamp 70 threadedly engaging threaded through-passage 75.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A spinal fixation device comprising:

a fastener having a head portion and a male shaft portion, wherein the outer surface of the shaft portion is threaded;

a connecting member having a female-tapered first through-passage formed therein, said connecting member further having internal sidewalls defining said first through-passage, said first through-passage tapering outwardly in a proximal-to-distal direction, said connecting member further comprising a second through-passage formed therein, the first through-passage and the second through-passage being configured and dimensioned to define a first axis and a second axis, respectively, wherein said first and second axes are not co-linear, and together cooperatively form an angle greater than zero degrees; and a fastening member configured and dimensioned to penetrate a pedicle, said fastening member having a male-tapered external portion that tapers outwardly in a proximal-to-distal direction, said male-tapered external portion having a female-threaded recess formed therein and being configured and dimensioned to mate with the sidewalls defining the first through-passage in frictional engagement therewith;

wherein the female-threaded recess is disposed in alignment with the second through-passage of the connecting member when the male-tapered external portion of the fastening member is disposed in engagement with the first through-passage of the connecting member, to thereby enable the fastener to pass through said second through-passage and into said female-threaded recess.

2. The spinal fixation device of claim 1, wherein the male-tapered portion has a first end a second end and is longer than the female-tapered first through-passage such that the second end of the male-tapered portion extends beyond said female-tapered first through-passage when said male-tapered portion is matingly engaged with the sidewalls defining the first through-passage in frictional engagement.

3. The spinal fixation device of claim 1, wherein the device further comprises an elongate support member, said support member having a bend formed therein such that said elongate support member has a first, longer portion and a second, shorter portion.

4. The spinal fixation device of claim 3, wherein the connecting member further comprises a gripping member having a concave sidewall defining an aperture formed therethrough allowing the elongate support member to pass through said aperture, wherein said gripping member grips said elongate support member and thereby locks said elongate support member in a location relative to the bone when said connecting member is in a clamped position.

5. The spinal fixation device of claim 1, the fastening member further comprises a first side and a second side with a mid collar separating the first side from the second side, the second side being threaded for attaching the fastening member to the bone.

6. The spinal fixation device of claim 1, wherein the connecting member further comprises a lower portion and an upper portion, the lower portion being configured and dimensioned such that said lower portion is at least twice the size of the upper portion.

7. The spinal fixation device of claim 1, the device further comprises an elongate support member and a stem member having a stem portion, the elongate support member and the stem portion having equal diameters such that one connecting member may be selectively attached to either said elongate support member or said stem portion.

8. The spinal fixation device of claim 1, the device having a disengaging means for disengaging and releasing the frictional engagement to thereby cause the release of said male-tapered external portion from said female-tapered first through-passage of the connecting member.

9. The spinal fixation device of claim 1, the device having a stem portion and an aligning means for aligning the fastening member and the stem portion to thereby cause said fastening member to be positioned in a substantially orthogonal position with respect to said stem portion when said fastening member is attached to the bone.

10. The spinal fixation device of claim 1, wherein the fastening member further comprises a head, said head being formed collectively of a first head portion and a second head portion.

11. The spinal fixation device of claim 10, wherein the first head portion may be configured as a cylindrical portion and formed on top of the second head portion, and wherein the second head portion may be configured as a tapered portion.

12. The spinal fixation device of claim 11, wherein the first head portion has a recess formed therein.

13. The spinal fixation device of claim 10, wherein the first head portion may be configured as a tapered portion and formed on top of the second head portion, and wherein the second head portion may be configured as a cylindrical portion.

14. The spinal fixation device of claim 13, wherein the first head portion has a recess formed therein.

15. The spinal fixation device of claim 1, wherein the fastening member further comprises a head, said head being formed collectively of a first head portion and a second head portion, both the first head portion and the second head portion being tapered.

16. The spinal fixation device of claim 1, wherein the fastening member further comprises a head, said head being formed collectively of a first head portion and a second head portion, both the first head portion and the second head portion being substantially cylindrical.

* * * * *